US00PP09461P

United States Patent [19]

Gentry

[11] Patent Number: Plant 9,461

[45] Date of Patent: Mar. 5, 1996

[54] BARBERRY PLANT 'GENTRY' CULTIVAR

[76] Inventor: Leo E. Gentry, 22835 SE. Tillstrom Rd., Gresham, Oreg. 97080

[21] Appl. No.: 295,412

[22] Filed: Aug. 23, 1994

[51] Int. Cl.[6] ..... A01H 5/00

[52] U.S. Cl. ..... Plt./58

[58] Field of Search ..... Plt./58

[56] References Cited

U.S. PATENT DOCUMENTS

P.P. 703 7/1946 De Groot ..... Plt./58

P.P. 1,968 8/1960 Crawford ..... Plt./58

P.P. 6,269 9/1988 de Wit ..... Plt./58

*Primary Examiner*—James R. Feyrer

*Attorney, Agent, or Firm*—Chernoff, Vilhauer, McClung and Stenzel

[57] ABSTRACT

A new and distinct variety of *Berberis thunbergii* is distinguishable from the closest known variety and from its parent due to the color of its leaves and by its ability to grow in full sun and with midday waterings without suffering sunburn or scald. Newly formed leaves have a rich blush burgundy color and are covered with a velvety pubescence that beads water like a freshly waxed car. As the leaves mature, they darken to a reddish-black satin patina.

1 Drawing Sheet

BACKGROUND AND SUMMARY OF THE INVENTION

The subject variety was discovered in 1989 growing in a bed of 15,000 containerized *Berberis thungbergii* Crimson Pygmy at the Leo Gentry Wholesale Nursery in Gresham, Oreg. The plants in this bed were propagated from vegetative cuttings taken from several thousand mature Crimson Pygmy plants growing at the nursery. All of the plants growing in this bed were from cuttings taken from Crimson Pygmy plants.

The new variety is distinguishable from other varieties of barberry due to the rich blush burgundy color of its leaves, which turn to a reddish-black satin patina as they mature. The variety also exhibits more resistance to sunburn and scald than other red-leaved varieties of barberry. Plants of the new variety have been asexually reproduced at Gresham, Oreg. using soft-wood cuttings. The characteristics of the new variety have been found to remain true when asexually reproduced, through multiple generations over a four-year period.

DETAILED DESCRIPTION OF THE VARIETY

Figure 1:
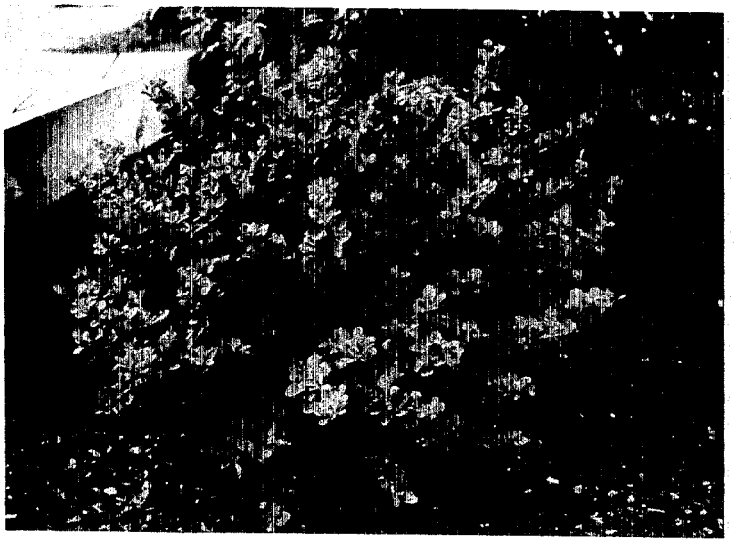
FIG. 1 is a recently planted one gallon-sized plant of the subject variety in a landscape setting showing the color of newly formed leaves.
Figure 2:
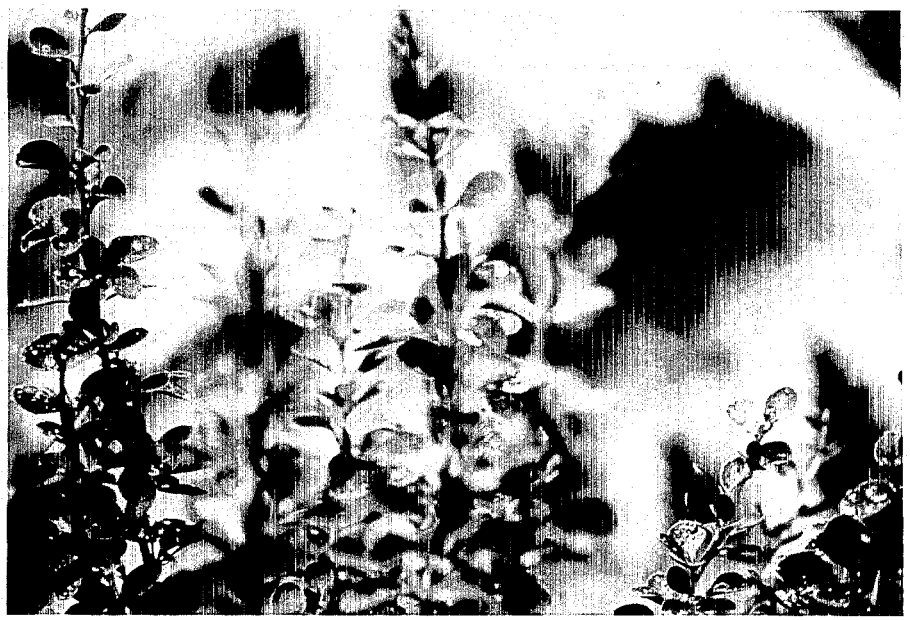
FIG. 2 is a close-up of the variety showing the color of mature leaves and showing the beading of water on the leaves.

The following description is based on plants growing at the Leo Genry Wholesale Nursery in Gresham, Oreg. Color references are to the Pantome Matching System, 1963, 1992.

The vegetative and reproductive parts of the new variety are, in most respects, typical of barberry plants. Its growth pattern and the size and shape of its leaves are similar to the Crimsom Pygmy barberry. The mature plant develops into a densely compact, low-mounding shrub, slightly smaller than the Crimson Pygmy, but similar in habit. It produces clusters of small yellow flowers followed by tiny red fruiting bodies that are typical of the genus.

Juvenile leaves of the subject variety are covered with a beautiful velvety pubescence that beads water drops like a freshly waxed car. The leaf develops as a superior and much richer blush burgundy (No. 504) than does Crimson Pygmy, then gradually darkens to a soft but showy, reddish-black satin patina (No. 439–440) as it fully matures. The leaves of Crimson Pygmy develop a reflective, waxy sheen which does not occur with the subject variety. The contrast between the two plants is readily noticeable at a glance under any lighting, but is especially pronounced in bright sunlight. The leaves of the subject variety retain their color throughout the propagation period, even in the shade, whereas the parent, Crimson Pygmy, washes out to a burnt orange color. Another particularly unique characteristic of the subject variety is that its leaves resist burning even in full sun. Blocks of plants were deliberately placed on a south aspect so they received maximum exposure to the hot afternoon sun. In spite of daily waterings and water drops standing on the tender young leaves, there was no apparent evidence of sunburn or scald. This is a distinct difference from Crimson Pygmy.

Stems of new growth are nearly identical in color to the blush burgundy of the leaves, but there is one botanically unique stem feature not seen in other red-leaved barberry. *Berberis thunbergii* typically has one spine at the base of each leaf node. The spine on the subject variety most commonly occurs in threes on the mature plant.

It is believed that the subject variety is cold-hardy to U.S.D.A. Cold-hardiness Zone 3.

Details of the subject variety in comparison with the parent variety and the closest known patented varieties are set forth in the following table: (The characteristics of the patented varieties are based on the patents and thus are limited to the disclosures made in the patents, as noted).

| SPECIFICATION | GENTRY CULTIVAR |
|---|---|
| Foliage | |
| Color | |
| Immature | Pantone #504. New leaves |

-continued

| | |
|---|---|
| | emerge burgundy both surfaces. Not glossy-distinctive flat "finish" |
| Mature | Pantone #439–440 w/hints of green to all green underside Not glossy-distinctive flat "finish" |
| Interior & Heavy Shade | Pantone #575-Dull green w/some splotches of red mature leaf color Not glossy-distinctive flat "finish" |
| Texture | Finely pubescent, both surfaces whitish under |
| Size & Shape | Obovate to Orbicular. Much more rounded that Crimson Pygmy. L × W = 0.75-1" × .6" |
| Margin | Smooth |
| Plant Growth | |
| Rate | 3-6"/yr at the location of plant culture in Gresham, OR |
| Form | Densely compact, low mounding. Expected to mature at about 2½' H × 3' W. Multiple upright basal branching. |
| Stems | Older stems woody. New growth emerges green w/red tinge, turning entirely red, then woody. |
| Spines | Spine is borne singly at first then most commonly occurs 3-parted |
| Internodal length | 0.4–0.6" at location of culture |
| Flowering Habit | Small red flowers followed by tiny red fruiting bodies are typical for the Genus |

| SPECIFICATION | CRIMSON PYGMY |
|---|---|
| Foliage | |
| Color | |
| Immature | Pantone #490. New leaves emerge crimson both surfaces. Highly glossy |
| Mature | Pantone #4975 w/hints of green to all green underside Hightly glossy |
| Interior & Heavy Shade | Pantone #574-Shiny green w/ some splotches of the mature red Highly glossy |
| Texture | Smooth, waxy, both surfaces-somewhat glaucous under |
| Size & Shape | Obovate to Spatulate-oblong More elongated L × W = 1.25" × |
| Margin | Smooth |
| Plant Growth | |
| Rate | Growth rate in similar conditions at Gresham, OR about twice that of Royal Burgundy |
| Form | Low, dense plant much wider than high. 1½' H × 2½–3' W Multiple upright basal branching. |
| Stems | Older growth woody. New growth green with reddish tips. |
| Spines | Usually has single spines |
| Internodal length | 0.4–0.6" at location of culture |
| Flowering Habit | Small yellow flowers, tiny red fruiting bodies |

-continued

| SPECIFICATION | DeGROOT PP 703 |
|---|---|
| Foliage | |
| Color | |
| Immature | Upper = Victoria Lake Plate 1 Under = corydalis Green Pl 41 |
| Mature | Upper = Hayes Maroom Plate 13 Under = Lt Grape Green Plate 41 |
| Interior & Heavy Shade | Not stated on patent |
| Texture | Leathery above, glauscent below |
| Size & Shape | Spatulate. About 1½" long |
| Margin | Not stated on patent |
| Plant Growth | |
| Rate | To 4' w/n 3 years |
| Form | Upright, ascending branches. To 4' w/n 3 years |
| Stems | Chestnut brown. Upright branches. |
| Spines | Simple spine at each leaf cluster |
| Internodal length | Not stated on patent |
| Flowering Habit | Inconspicuous yellow flower racemes. Oblong Nopal Red fruit. |

| SPECIFICATION | CRAWFORD PP 1969 | de WIT PP 6269 |
|---|---|---|
| Foliage | | |
| Color | | |
| Immature | Munsell Mod Red 2.5 R 4/10 | Munsell Brt Fuscia 5 RP 5/6-3-6 |
| Mature | Munsell Dk Red 2.5 R 3/7 | Munsell 7.5 P 4/2-2-2 w/lighter maroon veins |
| Interior & Heavy Shade | Not stated on patent | Not stated on patent |
| Texture | Not stated on patent | Glabrous |
| Size & Shape | Ovate. L × W = ½× 1" × ¼–1" | Broadly elliptical. L × W = 2" × 1–1½" |
| Margin | Not stated on patent | Sometimes serrated w/age |
| Plant Growth | | |
| Rate | Not stated on patent | Not stated on patent |
| Form | Spreading, dense Medium size | Fountain-like habit. Strong basal branching. Size not specified. |
| Stems | Mature wood is moderate yellowish-brown streaked w/ dark red. New growth, moderate red | Older stems cordovan brown. Immature twigs vary in color from deep magenta at the tip to brown at the base |
| Spines | Vary from simple to 3-parted | Not stated on patent |
| Internodal length | Not stated on patent | Not stated on patent |
| Flowering Habit | No flowers or fruit | Yellow flowers and red ellipsoidal fruit. |

What is claimed is:

1. A new and distinct variety of *Berberis thunbergii* substantially as shown and described, characterized particularly by the rich blush burgundy color of its newly-formed leaves which mature to a reddish-black satin patina, and by the resistance of the leaves to sunburn and scald.

* * * * *